United States Patent [19]
Yamamoto

[11] Patent Number: 5,854,029
[45] Date of Patent: Dec. 29, 1998

[54] METHOD FOR PREPARING ANTIHYPERTENSIVE AGENT

[75] Inventor: Naoyuki Yamamoto, Sagamihara, Japan

[73] Assignee: Calpis Co., Ltd., Tokyo, Japan

[21] Appl. No.: 900,899

[22] Filed: Jul. 25, 1997

[30] Foreign Application Priority Data

Aug. 2, 1996 [JP] Japan ................................. 8-204665

[51] Int. Cl.$^6$ ........................... C12P 21/02; A61K 38/05; C07K 5/06
[52] U.S. Cl. .......................... 435/71.2; 514/19; 530/800
[58] Field of Search ............................. 514/19; 530/800; 435/71.2

[56] References Cited

PUBLICATIONS

Maher, T., et al. Use of parenteral dipeptides to increase serum tyrosine levels and to enhance catecholamine–mediated neurotransmission. J. Pharm. Sci. 79(8):685–7, Aug. 1990.

Miyakawa, H., et al. Purification and characterization of an X–prolyl dipeptidyl aminopeptidase from *Lactobacillus helveticus* LHE–511. Milchwissenschaft. 49(12):670–3, Dec. 1994.

*Primary Examiner*—Cecilia J. Tsang
*Assistant Examiner*—Cecilia F. Wang
*Attorney, Agent, or Firm*—Darby & Darby

[57] ABSTRACT

An antihypertensive agent containing an effective amount of dipeptide Tyr-Pro and/or a pharmaceutically acceptable salt thereof, the effective amount being from 0.05 to 10 mg/kg body weight/day, and a method for producing the same.

6 Claims, No Drawings

METHOD FOR PREPARING ANTIHYPERTENSIVE AGENT

BACKGROUND OF THE INVENTION

The present invention relates to an antihypertensive agent containing as an active ingredient a dipeptide having antihypertensive effect, which agent may be utilized for medicine, foods for specified health use and healthy foods, and which agent exhibit the effect even in a small dose. The present invention also relates to a method for preparing such antihypertensive agent.

PRIOR ART

Angiotensin converting enzyme (ACE), having close relationship with manifestation of hypertension, exists mainly in lungs or angioendothelial cells. ACE is known to exhibit a strong hypertensive effect by cleaving angiotensin I produced by renin, to produce angiotensin II, a bioactive peptide which causes contraction of a smooth muscle of a blood vessel. In addition, ACE degrades and inactivates bradykinin which has antihypertensive effect. Accordingly, ACE has a hypertensive effect, and it is thus believed that blood pressure may be suppressed by inhibiting the activity of this enzyme.

There have been found substances having ACE inhibiting ability among various natural products or synthetic products. Some of such substances have already been put to practical use as an antihypertensive agent. For example, captopril (D-2-methyl-3-mercaptopropanoyl-L-proline) is a well-known synthetic chemical product having ACE inhibiting ability. However, special attention must be paid at all times to safety aspects of these synthetic chemical products.

As natural products, it has been reported that various anti ACE peptides are contained in milk protein, soybean protein or fish meat protein. These natural ACE inhibitory substances are proposed for practical use as antihypertensive agents having low toxicity and great safety. However, most of these antihypertensive peptide are contained only in small amount in such natural products and therefore sufficient effect cannot be expected in practical oral intake. In addition, most of the peptides do not have strong antihypertensive effect even if the peptides have strong ACE inhibition activity.

Recently, a report has been made on two tripeptides having strong ACE inhibiting activity, Val-Pro-Pro and Ile-Pro-Pro, derived from lactic acid bacteria-fermented milk (J. Dairy Sci. 78:777–783). Further, strong antihypertensive effect of these tripeptides has been confirmed in spontaneously hypertensive rats (SHR) (J. Dairy Sci. 78:1253–1257). However, since the tripeptides is produced by proteinase which is produced by lactic acid bacteria as lactic acid fermentation proceeds in milk, the resulting amount of tripeptides tends to vary depending on the conditions of fermentation. It is thus difficult to obtain the tripeptides in a stable amount.

It has also been reported that yogurt produced by lactic acid bacteria fermentation of milk as a raw material has antihypertensive effect (Japanese Laid-open Patent Application No.95–123977). However, the active substance for antihypertensive effect has yet been unknown.

Therefore, it is desired to provide a natural antihypertensive peptide, which is specified as an active substance, can be produced in an industrially stable manner, is effective in a small dose, and has greater safety.

SUMMARY OF THE INVENTION

It is an object of the present invention to provide an antihypertensive agent to be used for medicines, foods for specified health use and healthy foods, which is highly safe and is effective in oral dosage, and a method for producing the same.

It is another object of the present invention to provide an antihypertensive agent which is effective even in a low oral dosage, and a method for producing such agent by purifying the above-mentioned antihypertensive agent.

According to the present invention, there is provided an antihypertensive agent comprising an effective amount of peptides selected from the group consisting of a dipeptide Tyr-Pro, a pharmaceutically acceptable salt of the dipeptide Tyr-Pro, and mixtures thereof, said effective amount being from 0.05 to 10 mg/kg body weight/day.

According to the present invention, there is also provided a method for preparing the antihypertensive agent comprising the step of culturing lactic acid bacteria of the genus Lactobacillus with a medium containing a peptide and/or protein including an amino acid sequence Tyr-Pro, to obtain a cultured liquid containing dipeptide Tyr-Pro.

PREFERRED EMBODIMENTS OF THE INVENTION

The antihypertensive agent of the present invention contains an effective amount of dipeptide Tyr-Pro and/or a salt thereof. The salt may be enumerated by a pharmaceutically acceptable salt, including an inorganic acid salt, such as hydrochlorate, sulfate or phosphate, and an organic acid salt, such as citrate, maleate, fumarate, tartarate or lactate.

The antihypertensive agent of the present invention containing the dipeptide Tyr-Pro and/or the salt thereof as an active ingredient may be produced by a method of treating a food material containing a peptide and/or a protein including the amino acid sequence Tyr-Pro with a proteinase, or a publicly known organic synthesis. More preferably, the antihypertensive agent may be produced by culturing lactic acid bacteria, preferably lactic acid bacteria of the genus Lactobacillus, in a medium containing a peptide and/or a protein including the amino acid sequence Tyr-Pro, thereby obtaining a cultured liquid containing the dipeptide Tyr-Pro. That is, the dipeptide Tyr-Pro may be obtained by cultivation treatment of the medium with lactic acid bacteria, preferably lactic acid bacteria of the genus Lactobacillus.

The lactic acid bacteria of the genus Lactobacillus may include, for example, *Lactobacillus helveticus*, *Lactobacillus elbruekii* subsp. Bulgaricus, and *Lactobacillus acidophilus*. Of these, *Lactobacillus helveticus* is particularly preferred.

The medium is not particularly limited provided that the medium contains a peptide and/or a protein including amino acid sequence Tyr-Pro, and may include mediums derived from various food materials containing animal milk proteins such as animal whole milk, skim milk, and casein of an animal milk, and food materials containing vegetable proteins such as corn, corn protein, wheat, wheat protein, soybean, delipidized soybean and soybean protein; and commercially available mediums for lactic acid bacteria such as Briggs liver broth and MRS broth. Further, the medium may also be an aqueous solution containing natural food materials containing animal milk proteins and/or vegetable proteins including amino acid sequence Tyr-Pro, to which other mediums for lactic acid bacteria, a yeast extract, vitamins or minerals have optionally been added.

The culturing of the lactic acid bacteria may be performed by adding pre-cultured lactic acid bacteria starter to the medium which have been previously heat-sterilized and cooled to the predetermined temperature for incubation. The inoculation amount of the lactic acid bacteria starter may preferably be $10^5$ to $10^7$ cells of lactic acid bacteria/ml medium. The temperature for incubation is usually 20° to 50° C. and preferably 30° to 45° C. The incubation time is usually 3 to 48 hours and preferably 6 to 24 hours. Particularly, it is preferred to perform cultivation in the medium having pH in a range of 3.5 to 7, more preferably 4 to 5, in order to perform cultivation of lactic acid bacteria efficiently. Further, it is preferred to perform pH-stat cultivation maintaining pH in a range of 4 to 7. The incubation may be terminated, without restriction, when the number of lactic acid bacteria exceeds $10^8$ cells/ml.

Further, the cultured liquid containing dipeptide Tyr-Pro obtained by the aforementionedmethodmay be centrifuged, and the resulting supernatant may be subjected to purifying treatment with a reverse-phase resin, for obtaining an antihypertensive agent in which the content of the active ingredient, dipeptide Tyr-Pro, is increased.

The centrifugation may preferably be performed, for example, at 5,000 to 20,000 rpm for 1 to 10 minutes. The centrifugation may also be performed in a centrifugator.

The purifying treatment with a reverse-phase resin may be performed by absorption and elution of the dipeptide with a reverse-phase resin, and/or by reverse-phase chromatography, thereby increasing purity of dipeptide Tyr-Pro. The absorption and elution with the reverse-phase resin may be performed by, for example, treating the cultured liquid by a column method or a batch method with a resin such as "Preparative C18" (manufactured by WATERS INC.) as a reverse-phase resin, and then eluting the absorbed fraction with a polar solvent such as water, methanol, ethanol, 1-propanol, 2-propanol or acetonitrile, 25 preferably an aqueous solution containing 20 v/v % of acetonitrile, followed by evaporation of the solvent, for concentrating dipeptide Tyr-Pro.

The treatment by reverse-phase chromatography may be performed, without limitation, by publicly known reverse-phase high performance liquid chromatography (HPLC). HPLC may be performed by a linear gradient method using similar solvents to those enumerated in the absorption and elution with the reverse-phase resin, for obtaining dipeptide Tyr-Pro with high purity. The treatment by reverse-phase chromatography may be repeated plural times for further increasing the purity of the dipeptide Tyr-Pro.

The antihypertensive agent obtained by the method of the present invention is usually a mixture of peptides, and may contain other peptides than dipeptide Tyr-Pro. For use as foods and drinks, the cultured liquid containing the dipeptide Tyr-Pro and/or purified products thereof may be used directly. Alternatively, the agent may be powdered by freeze drying, spray drying or drum dryer drying, before use.

The effective amount of the antihypertensive agent of the present invention varies depending upon the age and condition of a patient, and is in a range of 0.5 to 10 mg/kg body weight/day. It is preferable to administer 0.3 to 3.0 mg/kg body weight/day. If the dose is not less than 0.05 mg/kg body weight/day, sufficient effect may be expected. If the dose is not more than 10 mg/kg body weight/day, the effect may be exhibited efficiently.

The dipeptide Tyr-Pro was orally administered to WKY rats showing normal blood pressure (18 weeks old, body weight of 320 g, n=5) in an amount of 10 mg/kg body weight/day continuously for one month, and no abnormality was found in behavior, appearance, blood pressure and autopsy of the rats. Foods fermented with Lactobacillus bacteria have been eaten by human beings for a long time, and it is therefore assumed that Tyr-Pro contained in the antihypertensive agent of the present invention has no problem in safety.

Since the antihypertensive agent of the present invention contains dipeptide Tyr-Pro as an active ingredient, it can reduce blood pressure in significantly low dose, compared with antihypertensive peptides derived from food materials reported to date. In addition, the antihypertensive agent of the present invention is highly safe, and thus can be used as medicine, foods for specified health use and healthy foods.

Since the method of the present invention includes culturing of lactic acid bacteria in a medium containing a peptide and/or a protein, the antihypertensive agent containing as an active ingredient dipeptide Tyr-Pro having great safety may be produced easily at low cost from a material such as natural peptides and proteins.

EXAMPLES OF THE INVENTION

The present invention will be explained in further detail with reference to Examples which are given only for illustration and are not intended for limiting the invention.

Preparation Example 1

10 kg of a 9 wt % aqueous solution of skim milk powders were inoculated with 300 g of fermented milk fermented with *Lactobacillus helveticus* CPN4 (FERM BP-4835) as a lactic acid bacteria starter. The inoculated solution was incubated at 37° C. for 8 hours. When curd was formed and the pH reached 4.2, the incubation was terminated and the solution was cooled. In the obtained fermented milk solution, 1.0 mg/100 g of dipeptide Tyr-Pro was contained.

10 kg of the obtained fermented milk solution were centrifuged at 10,000 rpm for 10 minutes, to retrieve 8.4 kg of whey. In the whey, 1.1 mg/100 g of dipeptide Tyr-Pro were contained.

*L. helveticus* CPN4 strain belongs to *L. helveticus*, and was deposited at National Institute of Bioscience and Human-Technology Agency of Industrial Science and Technology on Oct. 17, 1994, and has been accorded accession number FERM BP-4835. FERM BP-4835 has been accepted for deposit under the Budapest Treaty on the International Recognition of the Deposit of Microorganisms for the Purposes of Patent Procedure. All restrictions on the availability to the public of FERM BP-4835 will be irrevocably removed upon the granting of a patent.

Example 1

120 mg of the whey obtained in Preparation Example 1 were subjected to an absorption treatment through 10 seppak cartridges (WATERS INC.), and subsequently to an elution treatment under various conditions shown in Table 1 with an acetonitrile containing 0.1 wt % of TFA (trifluoroacetic acid) (solution B) diluted with an aqueous solution containing 0.1 wt % of TFA (solution A). A sample eluted without absorption and samples eluted under each condition were defined as Fractions 1 to 6, respectively. Each fraction was freeze-dried and dissolved in 40ml of physiological saline to prepare Samples 1 to 6.

The obtained whey before fractionation and Samples 1 to 6 were administered to spontaneously hypertensive rats (SHR: from CHARLES RIVER JAPAN INC., five rats per group, 20 to 22 weeks old, male) with a stomach sonde in an amount of 1 ml/animal. The change in the maximal blood pressure after six hours was compared with that of a control group to which physiological saline was administered. The measurement of blood pressure was performed by tail cuff method using a noninvasive blood pressure measurement apparatus (trade name "PE 300", NARKO BIO-SYSTEMS, CO.,LTD.). As a result, a significant antihypertensive effect was observed in Sample 2 as shown in Table 1. Therefore, Fraction 2 was found to be active.

TABLE 1

| Sample | Ratio of Solution B (%) | Blood Pressure Reduction After 6 hours (ΔSBP ± SE) |
|---|---|---|
| Before Fractionation | — | −29.6 ± 9.5*** |
| Fraction 1 | not absorbed | −9.6 ± 5.7* |
| Fraction 2 | 0–10 | −22.3 ± 3.2*** (Active Fraction) |
| Fraction 3 | 10–15 | −8.1 ± 2.6 |
| Fraction 4 | 15–20 | 1.0 ± 6.3 |
| Fraction 5 | 20–30 | −8.8 ± 8.5* |
| Fraction 6 | 30–50 | −7.6 ± 5.3 |
| Control (physiological saline) | | 1.9 ± 8.1 |

***; $P < 0.001$,
*; $P < 0.05$

Subsequently, Sample 2 was subjected to an elution treatment by reverse-phase high performance liqud chromatography (HPLC) under the following conditions according to the elution time shown in Table 2, to further fractionate Sample 2 into four Fractions 2-1 to 2-4. Application amount of Sample 2 in one elution was 1 ml, and elution was repeated 15 times. That is, a total of 15 ml of Sample 2 was fractionated.

Pump, L6200 INTELLIGENT pump manufactured by HITACHI LTD.;

Detector, L4000 UV detector manufactured by HITACHI LTD.;

Column, WATERS MICROBONDASPHERE 5μC18 manufactured by NIHON MILLIPORE LTD., Tokyo, Japan;

Eluent, Solution A (0.1 wt % aqueous solution of trifluoroacetic acid (TFA) ); and Solution B (acetonitrile containing 0.1 wt % of TFA);

Gradient, linear gradient from Solution B 0% (Solution A 100%) to Solution B 40% (Solution A 60%) (0 to 60 minutes) Flow rate, 1 ml/min.

Fractions 2-1 to 2-4 were freeze-dried, and dissolved in 15 ml of physiological saline to prepare Samples 2-1 to 2-4. These samples were orally administered to SHR with a stomach sonde in an amount of 1 ml/animal, and the change in the maximal blood pressure after six hours was compared with that of a control group to which physiological saline was administered, in the same manner as the above, in order to examine antihypertensive effect. As a result, a significant antihypertensive effect was observed in Fraction 2-2 as shown in Table 2. Therefore, Fraction 2-2 was found to be an active fraction.

TABLE 2

| Sample | Elution Time (min) | Blood Pressure Reduction After 6 hours (ΔSBP ± SE) |
|---|---|---|
| Fraction 2-1 | 10.5–16 | −13.0 ± 2.8** |
| Fraction 2-2 | 16–19 | −35.0 ± 9.7*** (Active Fraction) |
| Fraction 2-3 | 19–23 | −2.8 ± 5.3 |

TABLE 2-continued

| Sample | Elution Time (min) | Blood Pressure Reduction After 6 hours (ΔSBP ± SE) |
|---|---|---|
| Fraction 2-4 | 23–29 | −3.6 ± 5.6 |
| Control (physiological saline) | | 2.6 ± 6.0 |

***; $P < 0.001$,
**; $P < 0.01$ 1 ml of Sample 2-2 was subjected to elution treatment by the HPLC under the same conditions as those of the above except following the under-mentioned conditions:

Gradient, linear gradient from Solution B 5% (SolutionA 95%) to Solution B 20% (Solution A 80%) (0 to 60 minutes)

This elution was repeated ten times, that is, 10 ml in total of Samples 2-2 was subjected to the elution.

Each of the obtained Fractions 2-2-1 to 2-2-5 was freeze-dried and dissolved in 10 ml of physiological saline to prepare Sample 2-2-1 to 2-2-5. These samples were orally administered to SHR with a stomach sonde in an amount of 1 ml/animal, and the change in the maximal blood pressure after six hours was compared with that of a control group to which physiological saline was administered, in the same manner as the above, in order to examine antihypertensive effect. As a result, a significant antihypertensive effect was observed in Fraction 2-2-2 as shown in Table 3.

TABLE 3

| Sample | Elution Time (min) | Blood Pressure Reduction After 6 hours (ΔSBP ± SE) |
|---|---|---|
| Fraction 2-2-1 | 21.8 | −6.6 ± 5.5 |
| Fraction 2-2-2 | 22.7 | −23.0 ± 6.2*** (Active Fraction) |
| Fraction 2-2-3 | 24.0 | −9.0 ± 6.5* |
| Fraction 2-2-4 | 25.2 | −6.2 ± 6.2 |
| Fraction 2-2-5 | 25.8 | −3.5 ± 4.8 |
| Control (physiological saline) | | 2.6 ± 6.0 |

***; $P < 0.001$,
*; $P < 0.05$ 1 ml of Sample 2-2-2 was subjected to the elution treatment by the HPLC under the same conditions as those for treating Sample 2-2 for purifying the sample, and the amino acid sequence thereof from N-terminus was analyzed with "Automatic Protein Sequencer PPSQ-10 SYSTEM" manufactured by SHIMADZU CO. As a result, it was confirmed that amino acid sequence Tyr-Pro was contained. Alternatively, the purified peptide was hydrolyzed with 6N hydrochloric acid at the temperature of 105° C. for 24 hours, and amino acid analysis was performed with high-speed amino acid analysis system (trade name "Amino Acid Analysis System" manufactured by NIHON BUNKOU KOUGYO Co.). As a result, it was confirmed that amino acids Tyr and Pro were contained in equal moles. It was therefore concluded that the obtained peptide was a dipeptide having the sequence Tyr-Pro.

Preparation Example 2

100 kg of a 9 wt % aqueous solution of skim milk powders were inoculated with 3 kg of fermented milk fermented with *L. helveticus* CPN4 (FERM BP-4835), andculturedat 37° C. for 20 hours. The fermented milk solution thus obtained was treated in a Sharpless centrifugal separator at 10,000 rpm, to retrieve 78 kg of whey. Subsequently, the whey was applied to Preparative C18 packed column (3 litter capacity, manufactured by WATERS INC.). The column was then washed with 10 kg of a 5% aqueous solution of acetonitrile, followed by an elution treatment with 5 kg of a 10% aqueous solution of acetonitrile. The eluted fraction gave 1186 mg of freeze-dried product. This freeze-dried product contained 652 mg of dipeptide Tyr-Pro. The purity of the dipeptide Tyr-Pro was 55%.

Example 2

Antihypertensive effect of the fermented milk solution obtained in Preparation Example 1 was examined. Measurement of antihypertensive effect was performed utilizing SHR according to the method of Example 1. 4 ml/animal (12 ml/kg body weight) of the fermented milk solution or an unfermented milk solution was orally administered to SHR, and maximal blood pressure after six hours was measured. As a result, antihypertensive effect was confirmed. The results are shown in Table 4.

TABLE 4

| Sample | Blood Pressure Reduction After 6 hours (ΔSBP ± SE) |
|---|---|
| Unfermented Milk Solution | −3.5 ± 4.2 |
| CPN4 Fermented Milk Solution | −20.3 ± 5.2*** |

***; $P < 0.001$

Example 3

The antihypertensive peptide Tyr-Pro identified in Example 1 was solid-phase synthesized with an automatic peptide synthesizer PPSM-8 manufactured by SHIMADZU CO. The elution time of the obtained peptide Tyr-Pro on HPLC was the same as that of the peptide purified in Example 1.

Antihypertensive effect of the synthesized peptide was confirmed by the following method. 0.05, 0.1, 0.3, 1.0, 3.0 or 10 mg/kg body weight of the synthesized peptide Tyr-Pro was orally administered to SHR, and the maximal blood pressure after six hours was measured and compared with that of a control group to which physiological saline was administered, in the same manner as in Example 1. The results are shown in Table 5. From the results in Table 5, dose-dependent effect in a range of 0.05 to 3.0 mg/kg body weight was confirmed.

TABLE 5

| Amount of Tyr—Pro (mg/kg) | Blood Pressure Reduction After 6 hours (ΔSBP ± SE) |
|---|---|
| 10 | −32.1 ± 7.4*** |
| 3 | −30.5 ± 6.7*** |
| 1 | −27.4 ± 7.1*** |
| 0.3 | −20.8 ± 4.1*** |
| 0.1 | −10.2 ± 4.0* |
| 0.05 | −8.1 ± 3.3 |
| Control (physiological saline) | −3.6 ± 2.1 |

***; $P < 0.001$,
*; $P < 0.05$

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for preparing an antihypertensive agent containing an effective amount of peptides selected from the group consisting of a dipeptide Tyr-Pro, a pharmaceutically acceptable salt of the dipeptide Tyr-Pro, and mixtures thereof, wherein the method comprises culturing lactic acid bacteria of the genus Lactobacillus in a medium containing a peptide and/or protein comprising an amino acid sequence Tyr-Pro, to obtain a cultured liquid containing the dipeptide Tyr-Pro, wherein said effective amount of peptide ranges from 0.05 to 10 mg/kg body weight/day.

2. The method as claimed in claim 1 wherein said medium is selected from the group consisting of animal whole milk, animal skim milk, casein of animal milk, corn, corn protein, wheat, wheat protein, soybean, delipidized soybean, soybean protein, Briggs liver broth, MRS broth and mixtures thereof.

3. The method as claimed in claim 1 wherein said lactic acid bacteria of the genus Lactobacillus is *L. helveticus*.

4. The method as claimed in claim 1 wherein said culturing step is performed at 20° to 50° C. for 3 to 48 hours.

5. The method for preparing the antihypertensive agent as claimed in claim 1 wherein said culturing step is performed in the medium having pH in a range of 3.5 to 7.

6. The method as claimed in claim 1 further comprising the steps of centrifuging said cultured liquid containing dipeptide Tyr-Pro to obtain a supernatant, and purifying said supernatant with a reverse-phase resin.

* * * * *